United States Patent
Forbes et al.

(10) Patent No.: US 7,709,534 B2
(45) Date of Patent: May 4, 2010

(54) METHOD OF TREATING STRONGYLOIDES INFECTIONS AND MEDICAMENTS THEREFOR

(75) Inventors: Wayne M. Forbes, Upper Darby, PA (US); Ralph D. Robinson, Kingston (JM); Paul B. Reese, Kingston (JM)

(73) Assignee: University of the West Indies, Kingston (JM)

( * ) Notice: Subject to any disclaimer, the term of this patent is extended or adjusted under 35 U.S.C. 154(b) by 0 days.

(21) Appl. No.: 10/424,091

(22) Filed: Apr. 28, 2003

(65) Prior Publication Data

US 2004/0214900 A1    Oct. 28, 2004

(51) Int. Cl.
*A01N 35/00* (2006.01)
*A61K 31/11* (2006.01)

(52) U.S. Cl. ..................... 514/693; 514/703
(58) Field of Classification Search ............... 514/703, 514/693
See application file for complete search history.

(56) References Cited

U.S. PATENT DOCUMENTS 3,101,336 A * 8/1963 James et al. ............... 544/402
5,645,819 A * 7/1997 Klapow ...................... 424/45

OTHER PUBLICATIONS

Janssen et al. 101CA:235367, 1984.*
Janssen et al. 104CA:95238, 1985.*
Manowitz et al, 60CA:15004, 1964.*
Douglas et al. 136CA:35008, 2001.*
Cadwallader et al, 133CA:119221, 2000.*
Makarevich-Galperin et al, 49CA:74640, 1955.*
Cristea, et al., Derwent-ACC:1983-762956 as an English abstract of RO 81439.*
Mazza, Glacomo, "Minor volatile constituents of essential oil and extracts of coriander fruits" 2002, Sciences des Aliments, 22(5), 617-27.*
AFRD, "Coriander" 1998, Agri-Facts, Agdex 147/20-2, 1-4.*
Asprey, et al., "Medicinal Plants of Jamaica", W.I. Med. J., 2:233-252 (1953).
Ayensu, *Medicinal Plants of the West Indies* Reference Publications, Inc., Algonac, Michigan (1981) (18 pages).
Campbell, "Folk Lore and Food Habits", Jamaica Journal, 8(2 and 3):56-65 (1974).
Davis, et al., "Recent Studies on the Active Principles of Jamaican Medicinal Plants", W.I. Med. J., 19:101-110 (1970).
Halton, et al., "In Vitro Technique for Detecting Tegument Damage in Diclidophora Merlangi: Possible Screening Method for Selection of Undamaged Tissues or Organisms Prior to Physiological Investigation", Experimental Parasitology, 30:54-57 (1971).
Honychurch, Caribbean Wild Plants and Their Uses, (1980) (3 pages).
Lowe, "Jamaican Folk Medicine", Jamaica Journal, 6(2):20-24 (1972).
Robinson, et al., "Echinococcus Granulosus: Failure of the Cosin-Exclusion Test to Demonstrate Death of Protoscoleces", Annals of Tropical Medicine and Parasitology, 79(1):117 (1985).
Robinson, et al., "Inactivation of Strongyloides Stercoralis Filariform Larve in vitro by Six Jamaican Plant Extracts and Three Commercial Anthelmintics", W.I. Med. J., 36:213-217 (1990).

* cited by examiner

*Primary Examiner*—Yong S Chong
(74) *Attorney, Agent, or Firm*—Wilmer Cutler Pickering Hale and Dorr LLP

(57) ABSTRACT

Infections caused by parasitic nematodes of the genera *Strongyloides, Ancyclostoma, Necator, Haemonchus, Ascaris,* or *Trichuris* in humans and other mammals are treated by administration to an infected individual of an amount of a $C_8$-$C_{16}$-alpha,beta-unsaturated aliphatic aldehyde. Such compounds are useful for killing nematode worms of the genera listed above. A particularly useful compound of this class, effective against *S. stercoralis* infections, is E-2-dodecenal, having structural formula (1).

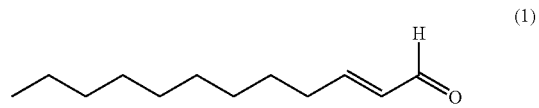

(1)

49 Claims, No Drawings

METHOD OF TREATING STRONGYLOIDES INFECTIONS AND MEDICAMENTS THEREFOR

BACKGROUND OF THE INVENTION

1. Field of the Invention

This invention relates to killing of nematodes (round worms and more particularly to treatment of infections caused by parasitic nematodes.

2. Brief Description of the Prior Art

*Strongyloides stercoralis* is an intestinal parasitic nematode infecting more than 100 million persons worldwide. It is the most common parasitic nematode that is able to recycle and proliferate within its host. Chronic, usually asymptomatic, gastrointestinal infections result in the majority of otherwise healthy individuals, but in immunocompromised hosts or persons receiving immunosuppressive therapy inordinate multiplication of the parasite follows with dissemination of larvae and adults to virtually all organs of the body. This is a grave and often lethal condition.

Other parasitic nematodes, for example, of the genera *Strongyloides, Ancyclostoma, Necator, Haemonchus, Ascaris*, and *Trichuris* are also medically significant pathogens in humans and other mammals. Infections with *Ascaris* species afflict some 1200 million persons worldwide, and *Trichuris* infections afflict some 800 million persons.

Treatment of disseminated strongyloidiasis with ethically prescribed pharmaceuticals has met with problems of poor efficacy and harmful side effects. To date, the benzimidazole group of drugs has proved the most valuable. Thiabendazole has remained the drug of choice for the last 30 years, but twin disadvantages of unreliable efficacy and significant toxicity generally call for a search for a more reliable and safe compound. Some investigations point to the potential usefulness of a broad-spectrum anthelmintic, albendazole, for the treatment of strongyloidiasis, whilst others argue the efficacy of ivermectin, a macrocyclic lactone produced by the actinomycete *Streptomyces avermitilis*.

The use of natural products in the treatment of intestinal helminths, which is venerated in Caribbean folklore, has received only limited attention. Reports and descriptions of such therapeutic uses may be found, for example, in Asprey & Thornton (1953) *West Ind Med J* 2:223-41; Davis & Persaud (1970) *West Ind Med J* 19:101-19; Lowe (1972) *Jamaica Journal* 8:20-4; Campbell (1974) *Jamaica Journal* 8:60-5; Honychurch (1980) *Caribbean Wild Plants and Their Uses*, Macmillan Press; Ayensu (1981) *Medicinal Plants of the West Indies*, Reference Pubs Inc.; Seaforth et al (1983) *A Guide to the Medicinal Plants of Trinidad*, Commonwealth Secretariat; McCallum (1985) *UWI Med. Biography*; Robinson et al (1990) *West Ind. Med J* 39: 213-7; Dias (1995) *Newsletter—G-15 Gene Banks* 718:4. About one hundred naturally occurring phytoproducts have been accredited with anthelmintic activity in vitro. On a wider scale, estimates indicate some 25,000 species of higher plants are used medicinally throughout the world where 80% of the population, most living in the tropic zones, rely heavily on traditional plant-based medications for health care. The potential of indigenous medicines is also recognised in the developed world, although to a much smaller extent. In the USA, for example, close to 100 secondary plant products have been incorporated as purified ingredients in more than 25% of prescribed preparations dispensed from the 1980's to the present time.

Accordingly, a need has continued to exist for the application of naturally occurring phytochemicals in the treatment of disease.

SUMMARY OF THE INVENTION

According to the invention infections caused by parasitic nematodes of the genera *Strongyloides, Ancyclostoma, Necator, Haemonchus, Ascaris*, and *Trichuris* in humans and other mammals are treated by administration to an infected individual of an amount of a $C_8$-$C_{16}$-alpha,beta-unsaturated aliphatic aldehyde. A particularly useful compound of this class is the compound of formula (1), i.e., E-2-dodecenal, as well as pharmaceutically acceptable solvates thereof.

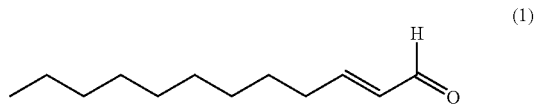

(1)

Susceptible nematodes are killed by exposure to a lethal amount of the above-described alpha,beta-unsaturated aldehyde.

Accordingly, it is an object of the invention to provide a method of killing nematodes.

A further object is to provide a method for treatment of infections with parasitic nematodes of the genera *Strongyloides, Ancyclostoma, Necator, Haemonchus, Ascaris*, and *Trichuris* in humans and other mammals.

A further object is to provide a method of treatment of infections with *Strongyloides stercoralis* in humans and other mammals.

A further object is to provide medicaments for treatment of infections with parasitic worms of the genera *Strongyloides, Ancyclostoma, Haemonchus, Ascaris*, and *Trichuris* in humans and other mammals.

A further object is to provide medicaments for treating infections with *Strongyloides stercoralis* in humans and other mammals.

A further object is to provide a method of killing parasitic worms of the genera *Strongyloides, Ancyclostoma, Haemonchus, Ascaris*, and *Trichuris*, and in particular *Strongyloides stercoralis*.

Further objects of the invention will become apparent from the description which follows.

DETAILED DESCRIPTION OF THE INVENTION AND PREFERRED EMBODIMENTS

According to the invention infections in humans and other mammals caused by parasitic worms of the genera *Strongyloides, Ancyclostoma, Necator*, and *Haemonchus* are treated and alleviated by administering to an individual infected with such a parasite an amount of a medium-chain $C_8$-$C_{16}$-alpha,beta-unsaturated aliphatic aldehyde effective to alleviate the infection.

A preferred class of alpha,beta-unsaturated aliphatic aldehydes comprises $C_{10}$-$C_{14}$-alpha,beta-unsaturated aliphatic aldehydes; and a preferred alpha,beta-unsaturated aliphatic aldehyde of the invention is E-2-dodecenal, having formula (1) above.

Those skilled in the art of organic chemistry will appreciate that many organic compounds form complexes (solvates) with solvents in which they are reacted, precipitated or crystallised. Solvates of the alpha,beta-unsaturated aliphatic aldehydes of the invention, and in particular of the compound of formula (1) are within the scope of the invention.

The alpha,beta-unsaturated aliphatic aldehydes of the invention may be isolated from plants such as coriander and the like or manufactured by conventional chemical synthesis methods.

According to the invention the alpha,beta-unsaturated aliphatic aldehydes are administered to an individual afflicted with strongyloidiasis in manner similar to that used for other conventional anthelmintic agents such as albendazole, thiabendazole, and ivermectin. However, Compound (1) has been found to be surprisingly rapid in action and of substantially greater potency than commercially available anthelmintic agents. Accordingly, the dosage and treatment regimen may be modified as indicated below.

The alpha,beta-unsaturated aliphatic aldehydes of the invention are useful in treatment of common intestinal strongyloidiasis as well as disseminated strongyloidiasis. They are also useful in treatment of other parasitic diseases such as malaria and other protistan infections, helmintic infections (e.g., hookworms, roundworms, etc.) and epizootic/ectoparasitic infections.

Parasitic nematodes of the genera *Strongyloides, Ancyclostoma, Necator, Haemonchus, Ascaris*, and *Trichuris* possess a system of amphidial neurons that exhibit functional, and structural similarities to the free-living nematode *Caenorhabditis elegans*, which has been extensively studied. Such parasitic worms include *Strongyloides stercoralis*, the threadworm of humans, other primates and dogs, *Ancyclostoma caninum*, the hookworm of dogs, *A. duodenale* and *Necator americanus*, hookworms of humans, and *Haemonchus contortus*, the stomach worm of ruminants. Homologs of amphidial neurons in *C. elegans* perform similar chemosensory and thermosensory functions in these parasitic nematodes and control their chemo- and thermosensory behavior. Upon exposure to the alpha,beta-unsaturated aldehydes used in the method of the invention, larvae of *S. stercoralis*, a representative parasitic worm of the class of parasites recited above, in contrast to their normal serpentine swimming movement, exhibit a 'twitching and vibrating' behavior prior to complete immobilization, indicating a likely neuromuscular effect of the active agent. The parasites rapidly become paralyzed and immobile, and then die. This behavior suggests that the active compound exercises its toxic effect on these parasites by a common mechanism affecting the operation of their neuromuscular system. The active compound may act on the amphidial neuron system of the parasites by affecting the release and/or availability of the neurotransmitter associated with these neurons, i.e., gamma-aminobutyric acid (GABA).

One skilled in the art will recognize that other parasitic nematodes, in addition to those of the genera enumerated above, have similar anatomy and physiology, and will be susceptible to killing by exposure to a lethal amount of the alpha,beta-unsaturated aldehydes of the invention.

The alpha,beta-unsaturated aliphatic aldehydes of the invention may be administered by any conventional route suitable for administration of anthelmintic pharmaceuticals. Oral, parenteral, and topical administration are appropriate, depending on the circumstances of the infection. For example, in treatment of parasites colonizing the proximal regions of the gut, i.e., the duodenum and small intestine, such as infection with *S. stercoralis*, oral administration is especially appropriate.

The amount of alpha,beta-unsaturated aliphatic aldehydes to be administered for effective treatment will, of course, vary with the individual organism being treated, the severity of the infection, and the like, and will be determined by the judgement and discretion of the medical or veterinary practitioner. Factors to be considered include the species of parasite involved, route of administration, nature of the dosage formulation, the organism's weight, age, reproductive and general condition. For a human patient, a suitable anthelmintic dose is in the range of about 0.001 mg/kg to about 2 mg/kg of body weight per day.

Daily doses may be administered as single or multiple doses, e.g., two to six times per day. Dosages above or below the range cited above are, of course, within the scope of the present invention and may be administered to the individual patient on the advice of the medical practitioner. For example, for a 75 kg mammal, a dose range would be about 0.4 mg to about 75 mg per day. If discrete multiple doses are indicated, treatment might typically be 2.5 mg of Compound (1) given 4 times per day.

Formulations

Formulations of the present invention for medical use comprise an active compounds, i.e., a $C_8$-$C_{16}$-alpha,beta-unsaturated aliphatic aldehyde, e.g., a compound of formula (1), together with a pharmaceutically acceptable carrier and/or other therapeutically active ingredients. The carrier preferably is an ethical pharmaceutical with the other ingredients of the formulation and not deleterious to the recipient.

The formulations include those appropriate for oral, topical and parenteral (including subcutaneous, intramuscular and intravenous) administration. Preference is given to those suitable for oral or parenteral administration.

The formulations may be presented in unit dosage form and may be prepared by any of the processes well known in the art of pharmacy. Essentially, the formulations are prepared by associating the active compound with a liquid or finely divided solid carrier and then, if necessary, forming the product into desired unit dosage form.

Formulations of the present invention suitable for oral administration may be discrete capsules, tablets or lozenges, each containing a predetermined amount of the active compound; or a suspension or solution in aqueous or non-aqueous liquid e.g., a syrup, an elixir, an emulsion or a draught.

A tablet may be made by compression or molding, optionally with one or more accessory ingredients. A syrup or suspension may be made by adding the active compound to a concentrated, aqueous solution of a sugar, e.g., sucrose, to which may also be added any accessory ingredients. Formulations suitable for parenteral administration conveniently comprise a sterile aqueous preparation of the active compound that is isotonic with the blood of the recipient. Topical formulations include ointments, gels, creams and lotions (which may also contain preservatives, perfumes, etc.), and may be prepared by standard methods well known in the art of pharmacy.

In addition to the aforementioned ingredients, the formulations of this invention may further include one or more optional accessory ingredients(s) utilised in the art of pharmaceutical formulations, e.g., diluents, buffers, flavoring agents, binders, surface active agents, thickeners, lubricants, suspending agents, preservatives (including antioxidants), and the like.

The invention will be illustrated by the following examples, which are intended in all respects to be illustrative and not limiting.

Example 1

This example illustrates the maintenance and culture of *S. stercoralis* in a laboratory environment for investigation and bioassay.

(i) Selection of Bioassay System

*S. stercoralis* presents a unique opportunity for investigators involved in screening novel compounds for antiparasitic biological activity. The possession of a heterogonic life cycle, whereby free-living adults produce large numbers of infective larvae in the external environment, uniquely lends this helminth to laboratory culture. Such laboratory culture has been used successfully by some of the inventors in Jamaica for more than 15 years to routinely screen and further study extracts of medicinal plants.

(ii) Maintenance of *S. stercoralis* in Mongrel Dogs

Two, fully weaned mongrel puppies were housed in a restricted access purpose-built kennel which allowed for adequate treatment (bleaching) and disposal of faeces. The animals were treated for ecto- and endoparasites using ethical enteric and topically applied chemotherapeutics. Weekly faecal samples were examined for helminth infections; when four consecutive negative findings occurred, the animals were considered helminth-free and ready for inoculation with *S. stercoralis* larvae.

Filariform larvae were harvested from agar cultures of faeces of an infected human volunteer. Larvae were maintained in Locke's nematode saline solution (LNSS) containing 400 i.u./mL benzyl penicillin and 400 i.u./mL streptomycin sulfate. Each dog was inoculated subcutaneously in the scruff area with 1 mL LNSS containing about 3,000 larvae. Daily oral administration of prednisolone (0.5 mg/kg) was required to maintain the infection. The prepatent period in mongrel dogs is typically 7-10 weeks.

(iii) Culture of *S. stercoralis* for Bioassay Work

Coproculture of about 30 g of fresh, moistened canine faeces was conducted using granular charcoal (1:1 v:v) in sealed 10 cm diameter Petri dishes. Cultures were maintained at 26° C. under semi-lighted conditions. *S. stercoralis* filariform larvae typically migrated to the surface of the culture and eventually into water droplets that condensed on the inner surface of the lid. Larvae appearing within 2 days were mostly those accruing from the homogonic cycle and usually occurred in insufficient numbers for bioassay. After five to eight days had elapsed free-living adult worms had effected a 50-fold increase in the population density (heterogonic cycle).

Example 2

This example illustrates the assay of effectiveness of Compound (1) in comparison with commercial anthelmintics.

The effectiveness of the tested compounds was evaluated by incubating larvae obtained as in Example 1 in suspensions containing 0.6% of Compound (1) as the active ingredient (AI). Incubation times were 1, 2, 3, 4, 5, 6, 24, 48, 72, and 96 hours. Three (3) replicates were run in each assay, using >>100 larvae per replicate.

The anthelmintic effectiveness of Compound (1) and of three commercial anthelmintics, namely albendazole, thiabendazole, and ivermectin, was evaluated, and the results are summarized in Table 1. Compound (1) immobilized 100% of the larvae within one hour's exposure. This was also true for ivermectin. However, similar concentrations of albendazole and thiabendazole immobilized 50% of the infective larvae only after 73.7 and 78.9 hours, respectively.

TABLE 1

Immobilisation times ($It_{50}$ in hours) of Compound (1) and commercial drugs (0.6% Active Ingredient (AI)) for *Strongyloides stercoralis* infective larvae.

| Agent (0.6% AI) | $It_{50}$ (hours) ±95% Fiducial limits (FL) | Regression equation ($Y = a + bx$) | | | Relative activity (RA) |
|---|---|---|---|---|---|
| | | a | b | (SE) | |
| Compound (1) | <1* | | | | >1.00 |
| Ivermectin | <1* | | | | >1.00 |
| Albendazole** | 73.7 (60.4-87.0) | −5.09 | 2.74 | (0.36) | 1.00 |
| Thiabendazole | 78.9 (65.5-92.8) | −12.02 | 6.27 | (0.75) | 0.93 |

*Limits could not be calculated from data
**RA of albendazole is used as a reference for other anthelmintic agents Example 3

This example illustrates the lethality of Compound (1) in comparison with commercial anthelmintics.

The lethality of the tested compounds was evaluated by incubating larvae obtained as in Example 1 in suspensions containing 0.6% of Compound (1) as the active ingredient (AI). The mortality time ($Lt_{50}$) for each active compound was determined, the results are summarized in Table 2.

The mortality of the larvae was assessed by a dye exclusion test such as have been used successfully to indicate viability in parasitic platyhelminths. (See Halton & Arme (1971) *Exp. Parasit.* 30:54; Robinson & Arme (1985) *Ann. Trop. Med. & Parasit.* 79:17.) Similar testing was applied to *S. stercoralis* larvae. In these tests, use of 0.01% v/v eosin in LNSS (ELNSS) in an eosin-exclusion test indicated death of larvae in less than 10 minutes and had no effect on healthy individuals.

The order of lethal activity using $Lt_{50}$ in hours for 0.6% (AI) suspensions of the anthelmintic agents is shown in Table 2: Compound (1), 2.2 h>ivermectin, 15.7 h>albendazole, 145.3 h>thiabendazole, 178.9 h. Compound (1) was significantly more potent than the commercial drugs. displaying a 7.1-, 66.1- and 81.3-fold increase in activity over ivermectin, albendazole and thiabendazole, respectively. Compound (1) killed 90.8% of the larvae after six hours, whereas ivermectin effected 89.0% mortality only after 24 hours. Albendazole and thiabendazole killed 37.4% and 14.1% of the larvae only after 120 hours, respectively.

TABLE 2

Mortality times ($Lt_{50}$ in hours) of Compound (1) and commercial drugs (0.6% AI) for *Strongyloides stercoralis* infective larvae.

| Agent 0.6% AI | $Lt_{50}$ (hours) ±95% Fiducial limits (FL) | Regression equation ($Y = a + bx$) | | | Relative activity (RA) |
|---|---|---|---|---|---|
| | | a | b | (SE) | |
| Compound(1) | 2.2 (1.2-3.3) | −10.62 | 4.92 | (1.17) | 1.00* |
| Ivermectin | 15.7 (12.5-18.1) | −7.35 | 2.94 | (1.72) | 0.14 |
| Albendazole | 145.3 (127.5-194.9) | −1.36 | 4.00 | (0.37) | 0.02 |
| Thiabendazole | 178.9 (155.9-229.0) | −31.37 | 23.62 | (1.2E+7) | 0.01 |

*RA of Compound (1) is used as a reference for other anthelmintic agents

Example 4

This example illustrates the preparation of oral tablets.
For preparation of 1000 tablets the following ingredients are used.

| Ingredients | Amount |
| --- | --- |
| Active Compound, i.e., compound of formula (1) | 20 g |
| Starch | 20 g |
| Magnesium Stearate | 1 g |

The active compound and the starch are granulated with water and dried. Magnesium stearate is added, and the mixture thoroughly blended and compressed into tablets.

Example 5

This example illustrates the preparation of capsules.
For preparation of 1000 capsules the following ingredients are used.

| Ingredients | Amount |
| --- | --- |
| Active Compound, i.e., compound of formula (1) | 20 g |
| Lactose | 450 g |
| Magnesium stearate | 5 g |

The finely ground active compound is mixed with the lactose and stearate and packed into gelatin capsules.

Example 6

This example illustrates the preparation of ampoules.
For preparation of 1000 ampoules for parenteral administration the following ingredients are used.

| Ingredients | Amounts |
| --- | --- |
| Active Compound, i.e., compound of formula (1) | 5 g |
| Buffering Agents | q.s. |
| Propylene glycol | 400 mg |
| Water for injection | 600 mL |

The active compound and buffering agents are dissolved in propylene glycol (at about 50° C.). The water for injection is then added with stirring and the resulting solution filtered, filled into ampoules, sealed and autoclaved (sterilized).

The invention has been described above in terms of preferred embodiments, in particular with reference to parasitic nematodes. However, the skilled practitioner will recognize that the invention is also applicable with reference to all nematodes susceptible to the disclosed active agent. Furthermore, it will be understood by those skilled in the art that various changes and modifications can be made without departing from the invention, and all such changes and modifications are intended to be included within the scope of the invention as defined in the appended claims.

We claim:

1. A method of treating mammals infected with a parasite of the genus *Strongyloides, Ancyclostoma, Necator, Haemonchus, Ascaris*, or *Trichuris*, comprising administering to said mammal $C_8$-$C_{16}$-alpha,beta-unsaturated aliphatic aldehyde, extracted from plant sources or chemically synthesized, and in an amount effective to alleviate said infection.

2. The method of claim 1, wherein said mammal is a human.

3. The method of claim 1, wherein said $C_8$-$C_{16}$-alpha,beta-unsaturated aliphatic aldehyde is a $C_{10}$-$C_{14}$-alpha,beta-unsaturated aliphatic aldehyde.

4. The method of claim 1, wherein said alpha,beta-unsaturated aliphatic aldehyde is E-2-dodecenal.

5. The method of claim 4, wherein said mammal is a human.

6. The method of claim 1, wherein said parasite is of the genus *Strongyloides*.

7. The method of claim 6, wherein said parasite is *Strongyloides stercoralis*.

8. The method of claim 7, wherein said mammal is a human.

9. The method of claim 8, wherein said $C_8$-$C_{16}$-alpha,beta-unsaturated aliphatic aldehyde is administered orally.

10. The method of claim 7, wherein said alpha,beta-unsaturated aliphatic aldehyde is E-2-dodecenal.

11. The method of claim 10, wherein said mammal is a human.

12. The method of claim 11, wherein said E-2-dodecenal is administered orally.

13. A method of killing a parasitic nematode worm of the genus *Strongyloides, Ancyclostoma, Necator, Haemonchus, Ascaris*, or *Trichuris*, comprising contacting said worm with $C_8$-$C_{16}$-alpha,beta-unsaturated aliphatic aldehyde, extracted from plant sources or chemically synthesized, and in an amount effective to kill said worm.

14. The method of claim 13, wherein said parasitic nematode is of the genus *Strongyloides*.

15. The method of claim 13, wherein said $C_8$-$C_{16}$-alpha,beta-unsaturated aliphatic aldehyde is a $C_{10}$-$C_{14}$-alpha,beta-unsaturated aliphatic aldehyde.

16. The method of claim 13, wherein said alpha,beta-unsaturated aliphatic aldehyde is E-2-dodecenal.

17. The method of claim 14, wherein said parasite is *Strongyloides stercoralis*.

18. The method of claim 16, wherein said parasite is *Strongyloides stercoralis*.

19. A method of treating a mammal infected with a parasite of the genus *Strongyloides, Ancyclostoma, Necator, Haemonchus, Ascaris*, or *Trichuris*, comprising
    determining that said mammal is infected with a parasite of the genus *Strongyloides, Ancyclostoma, Necator, Haemonchus, Ascaris*, or *Trichuris*, and
    administering to said infected mammal $C_8$-$C_{16}$-alpha,beta-unsaturated aliphatic aldehyde, extracted from plant sources or chemically synthesized and in an amount effective to alleviate said infection.

20. The method of claim 19, wherein said mammal is a human.

21. The method of claim 19, wherein said $C_8$-$C_{16}$-alpha,beta-unsaturated aliphatic aldehyde is a $C_{10}$-$C_{14}$-alpha,beta-unsaturated aliphatic aldehyde.

22. The method of claim 19, wherein said alpha,beta-unsaturated aliphatic aldehyde is E-2-dodecenal.

23. The method of claim 22, wherein said mammal is a human.

24. The method of claim 19, wherein said parasite is of the genus *Strongyloides*.

25. The method of claim 24, wherein said parasite is *Strongyloides stercoralis*.

26. The method of claim 25, wherein said mammal is a human.

27. The method of claim 26, wherein said $C_8$-$C_{16}$-alpha,beta-unsaturated aliphatic aldehyde is administered orally.

28. The method of claim 25 wherein said alpha,beta-unsaturated aliphatic aldehyde is E-2-dodecenal.

29. The method of claim 28, wherein said mammal is a human.

30. The method of claim 29, wherein said E-2-dodecenal is administered orally.

31. A method of treating mammals infected with a parasite of the genus *Strongyloides, Ancyclostoma, Necator, Haemonchus, Ascaris*, or *Trichuris*, comprising administering to said mammal a pharmaceutical composition consisting essentially of $C_8$-$C_{16}$-alpha,beta-unsaturated aliphatic aldehyde and a pharmaceutically acceptable carrier, in an amount effective to alleviate said infection.

32. The method of claim 31, wherein said $C_8$-$C_{16}$-alpha,beta-unsaturated aliphatic aldehyde is a $C_{10}$-$C_{14}$-alpha,beta-unsaturated aliphatic aldehyde.

33. The method of claim 31, wherein said alpha,beta-unsaturated aliphatic aldehyde is E-2-dodecenal.

34. The method of claim 33, wherein said mammal is a human.

35. The method of claim 34, wherein said parasite is of the genus *Strongyloides*.

36. The method of claim 35, wherein said parasite is *Strongyloides stercoralis*.

37. The method of claim 36, wherein said E-2-dodecenal is administered orally.

38. The method of claim 1, wherein said effective amount is within a range from about 0.001 mg/kg to about 2 mg/kg of body weight per day.

39. The method of claim 1, wherein said effective amount is within a range from about 0.005 mg/kg to about 1 mg/kg of body weight per day.

40. The method of claim 1, wherein said effective amount is about 0.033 mg/kg of body weight given 4 times per day.

41. The method of claim 19, wherein said effective amount is within a range from about 0.001 mg/kg to about 2 mg/kg of body weight per day.

42. The method of claim 19, wherein said effective amount is within a range from about 0.005 mg/kg to about 1 mg/kg of body weight per day.

43. The method of claim 19, wherein said effective amount is about 0.033 mg/kg of body weight given 4 times per day.

44. The method of claim 13, wherein said effective amount is within a range from about 0.001 mg/kg to about 2 mg/kg of body weight per day.

45. The method of claim 13, wherein said effective amount is within a range from about 0.005 mg/kg to about 1 mg/kg of body weight per day.

46. The method of claim 13, wherein said effective amount is about 0.033 mg/kg of body weight given 4 times per day.

47. The method of claim 31, wherein said effective amount is within a range from about 0.001 mg/kg to about 2 mg/kg of body weight per day.

48. The method of claim 31, wherein said effective amount is within a range from about 0.005 mg/kg to about 1 mg/kg of body weight per day.

49. The method of claim 31, wherein said effective amount is about 0.033 mg/kg of body weight given 4 times per day.

* * * * *